(12) United States Patent
Waller et al.

(10) Patent No.: US 9,458,217 B2
(45) Date of Patent: Oct. 4, 2016

(54) METHODS OF MANAGING GRAFT VERSUS HOST DISEASE

(71) Applicant: EMORY UNIVERSITY, Atlanta, GA (US)

(72) Inventors: Edmund K. Waller, Atlanta, GA (US); Cynthia R. Giver, Decatur, GA (US); Sravanti Rangaraju, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 14/561,275

(22) Filed: Dec. 5, 2014

(65) Prior Publication Data

US 2015/0158925 A1 Jun. 11, 2015

Related U.S. Application Data

(60) Provisional application No. 61/912,098, filed on Dec. 5, 2013.

(51) Int. Cl.

| | |
|---|---|
| A61K 38/22 | (2006.01) |
| A61K 38/16 | (2006.01) |
| C07K 14/575 | (2006.01) |
| A61K 35/28 | (2015.01) |
| A61K 45/06 | (2006.01) |
| A61N 5/10 | (2006.01) |
| A61K 31/337 | (2006.01) |

(52) U.S. Cl.
CPC ....... *C07K 14/57563* (2013.01); *A61K 31/337* (2013.01); *A61K 35/28* (2013.01); *A61K 38/2278* (2013.01); *A61K 45/06* (2013.01); *A61N 5/10* (2013.01)

(58) Field of Classification Search
None
See application file for complete search history.

(56) References Cited

U.S. PATENT DOCUMENTS

| | | | | |
|---|---|---|---|---|
| 5,217,953 A * | 6/1993 | Gozes | ............. | C07K 14/57563 514/17.7 |
| 5,565,424 A * | 10/1996 | Gozes | ............. | C07K 14/57563 435/7.2 |
| 6,492,330 B1 * | 12/2002 | Mukherjee | ............. | A61K 38/08 514/13.3 |
| 6,630,124 B1 * | 10/2003 | Gozes | .................... | A61K 38/14 424/1.11 |
| 6,828,304 B1 | 12/2004 | Burman | | |
| 6,911,430 B2 * | 6/2005 | Gandhi | ................. | A61K 38/25 424/185.1 |
| 7,094,755 B2 | 8/2006 | Burman | | |
| 2003/0158110 A1 | 8/2003 | Burman | | |
| 2010/0062004 A1 | 3/2010 | Adams | | |
| 2013/0130379 A1 | 5/2013 | Adams | | |
| 2013/0302351 A1 | 11/2013 | Waller et al. | | |

FOREIGN PATENT DOCUMENTS

| | | |
|---|---|---|
| WO | 2007104493 | 9/2007 |
| WO | 2009039991 | 4/2009 |
| WO | 2012111997 | 8/2012 |

OTHER PUBLICATIONS

Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
Wang et al 2001. J. Biol Chem. 276:49213-49220.*
Bowie et al. "Deciphering the Message in Protein Sequences: Tolerance to Amino Acid Substitutions" Science, 1990; 247: 1306-1310.
Chorny et al. "Vasoactive intestinal peptide induces regulatory dendritic cells that prevent acute graft-versus-host disease while maintaining the graft-versus-tumor" Blood, 2006; 107(9): 3787-3794.
Emilie et al. "Vasoactive intestinal peptide receptor 1 is downregulated during expansion of antigen-specific CD8 T cells following primary and secondary Listeria monocytogenes infections" J Neuroimmunol., 2011; 234(1-2): 40-48.
Fang et al. "A Convenient Approach to Synthesizing Peptide C-Terminal N-Alkyl Amides" Biopolymers, 2011; 96(6): 715-722.
Gonzalez et al. "Vasoactive intestinal peptide and regulatory T-cell induction: a new mechanism and therapeutic potential for immune homeostasis" Trends in Molecular Medicine, 2007; 13(6): 241-251.
Hossain et al. "Chronic GvHD decreases antiviral innnune responses in allogeneic BMT" Blood, 2007; 109: 4548-4556.
Kamar et al. "Predictive factors for cytomegalovirus reactivation in cytomegalovirus-seropositive kidney-transplant patients" J Med Virol., 2008; 80(6): 1012-1017.
Kordasti et al. "Serotonin and vasoactive intestinal peptide antagonists attenuate rotavirus diarrhoea" Gut, 2004; 53: 952-957.
Li et al. "Blocking Vasoactive Intestinal Peptide Signaling Enhances Anti-Viral Immunity without Increased Graft Versus Host disease in Murine Allogeneic Bone Marrow Transplantation" 53rd Annual Meeting and Exposition of the American-Society-of-Hematology (ASH), San Diego, 2011.
Li et al. "The Absence of Vasoactive Intestinal Peptide Augments Alloreactivity and The Anti-Viral Response in a Bone Marrow Transplant Setting" Biology of Blood and Marrow Transplantation, 2010; 1(2): S223-S224.
Li et al. "Absence of Vasoactive Intestinal Peptide Expression in Hematopoietic Cells Enhances Th1 Polarization and Antiviral Immunity in Mice" J Immunol, 2011; 187: 1057-1065.
Li et al. "Pharmacological inhibition of VIP signaling enhances antiviral immunity and improves survival in murine aytomegalovirus-infected allogeneic bone marrow transplant recipients" Blood, 2013; 121(12): 2347-2351.
Li et al. "VIPhyb, an Antagonist of Vasoactive Intestinal Peptide Receptor, Enhances Cellular Antiviral Immunity in Murine Cytomegalovirus Infected Mice" PLoS One, 2013; 8(5): e63381.
Lilja et al. "The next generation recombinant human cytomegalovirus vaccine candidates-beyond gB" Vaccine, 2012; 30(49): 6980-6990.

(Continued)

*Primary Examiner* — Shulamith H Shafer
(74) *Attorney, Agent, or Firm* — Emory Patent Group (57) ABSTRACT

This disclosure relates to the use of drugs to prevent graft versus host disease (GVHD) in a subject after, before, or during a hematopoietic stem cell transplant. In certain embodiments, the drugs are antagonist of vasoactive intestinal peptide signaling. In certain embodiments, the subject has a blood or bone marrow cancer or condition.

5 Claims, 3 Drawing Sheets

(56) References Cited

OTHER PUBLICATIONS

Moody et al. "(Stearyl, Norleucine17)VIP hybrid antagonizes VIP receptors on non-small cell lung cancer cells" Life Sciences, 1997; 61(17): 1657-1666.

Onoue et al. "Structure-activity relationship of vasoactive intestinal peptide (VIP): potent agonists and potential clinical applications" Arch Pharmacol., 2008; 377: 579-590.

Peruzzi et al. "Inhibition of Natural Killer Cell Cytotoxicity and Interferon γ Production by the Envelope Protein of HIV and Prevention by Vasoactive Intestinal Peptide" AIDS Res Hum Retroviruses, 2000; 16(11): 1067-1073.

Redwine et al. "Peptide T BLocks GP120/CCR5 Chemokine Receptor-Mediated Chemotaxis" Clinical Immunology, 1999; 93(2): 124-131.

Southerland et al. "The Absence of Vasoactive Intestinal Peptide Augments Allo-Reactivity and the Anti-Viral Response in Bone Marrow Transplantation" Blood, 2007; 110(11): 3267.

Thermo Electron Corporation "N-Terminal Acetylation and C-Terminal Amidation of Peptides" 2004, www.thermo.com/biopolymers.

Waller "Antagonism of vasoactive intestinal peptide activity stimulates anti-viral Immunity and protects transplant recipients from murine cytomegalovirus Infection" 37TH Annual Meeting of the European Group for Blood and Marrow Transplantaion, 2011.

Wang et al. "A Single Amino Acid Determines Lysophospholipid Specificity of the S1P1 (EDG1) and LPA1 (EDG2) Phospholipid Growth Factor Receptors" J. Biol Chem. 2001; 276: 49213-49220.

Wang et al. "Mechanisms of antigen presentation to T cells in murine graft-versus-host disease: cross-presentation and the appearance of cross-presentation" Blood, 2011; 118(24): 6426-6437.

Wells "Additivity of mutational effects in proteins" Biochemistry, 1990; 29(37): 8509-8517.

White et al. "Proteins, Peptides and Amino Acids" SourceBook, 2002; 435-437.

Yewdel et al. "Cross—dressers turn on T cells" Nature, 2011; 471(7340): 581-582.

Yuan et al. "Breaking Human Cytomegalovirus Major Immediate-Early Gene Silence by Vasoactive Intestinal Peptide Stimulation of the Protein Kinase A-CREB-TORC2 Signaling Cascade in Human Pluripotent Embryonal NTera2 Cells" Journal of Virology, 2009; 83(13): 6391-6403.

Zhilinskaia et al. "Detection in the structure of influenza viral proteins of sequences similar to vasoactive intestinal peptide" Biulleten Eksperimentalnoi Biologii I Meditsiny, Apr. 1991; 111(4): 371-373.

* cited by examiner

METHODS OF MANAGING GRAFT VERSUS HOST DISEASE

CROSS REFERENCE TO RELATED APPLICATIONS

This Application claims priority to U.S. Provisional Application No. 61/912,098 filed Dec. 5, 2013, hereby incorporated by reference in its entirety.

BACKGROUND

Certain stem cells and T cells originate in bone marrow and circulated in the blood. One option for treating cancers of the blood and bone marrow is to kill existing cells, e.g., through radiation or chemotherapy, and transplant similar cells from a healthy donor, referred to as an allogeneic hematopoietic stem cell transplant (allo-HSCT). A major complication of allo-HSCT is graft versus host disease (GVHD). Thus, there is a need to identify improved methods of preventing GVHD.

SUMMARY

This disclosure relates to the use of drugs to manage graft versus host disease (GVHD) in a subject after a hematopoietic stem cell transplant. In certain embodiments, the drugs are antagonist of vasoactive intestinal peptide signaling. In certain embodiments, the subject has a blood or bone marrow cancer or condition.

In certain embodiments, the disclosure relates to methods of treating or preventing host verses graft disease in a subject comprising administering an effective amount of an antagonist of vasoactive intestinal peptide signaling to a subject that is to receive or received transplanted allogeneic tissue or cells.

In certain embodiments, the subject received transplanted allogeneic hematopoietic stem cells. In certain embodiments, subject received transplanted allogeneic hematopoietic stem cells separated from peripheral blood. In certain embodiments, the subject received chemotherapy and/or radiation treatments prior to receiving transplanted allogeneic hematopoietic stem cells. In certain embodiments, the subject is a human.

In certain embodiments, the disclosure relates to methods of treating cancers or conditions of the blood and bone marrow comprising the steps of, exposing the subject to radiation and/or administering a chemotherapy agent to the subject; transplanting allogeneic hematopoietic stem cells into the subject; and administering an antagonist of vasoactive intestinal peptide signaling under conditions such that host verses graft disease is prevented or reduced. In certain embodiments, the cancer or conditions are selected from leukemia, lymphoma, myeloma, and myelodysplasia. In certain embodiments, the cancers or conditions are selected from osteosarcoma, Ewing tumors, chordomas, chondrosarcomas, bone marrow failure, sickle cell disease, and thalassemia.

BRIEF DESCRIPTIONS OF THE FIGURES

FIG. 4A shows data indicating that the additional of VIPhyb to allo-transplant recipients does not increase GvHD. The B16→B10.BR MHC-fully mis-matched allogeneic transplant model was used. Recipient mice received myeloablative conditioning with two fractions of 5.5 Gy TBI separated by three hours on day −2. On day 0 transplant recipients received 5 million T-cell depleted bone marrow cells in combination with 1, 3, or 8 million donor splenocytes from B6 WT or B6 VIP-KO mice. A separate group was transplanted with 5 million T-cell depleted bone marrow cells in combination with 1 million donor splenocytes from WT mice. Starting on day −1, and continuing daily through day +5, transplant recipients were treated with subcutaneous injections of 100 uL PBS or PBS containing 10 ug VIPhyb peptide. Transplant recipients were monitored daily for survival.

DETAILED DISCUSSION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

In certain embodiments, a pharmaceutical agent, which may be in the form of a salt or prodrug, is administered in methods disclosed herein that is specified by a weight. This refers to the weight of the recited compound. If in the form of a salt or prodrug, then the weight is the molar equivalent of the corresponding salt or prodrug.

It must be noted that, as used in the specification and the appended claims, the singular forms "a," "an," and "the" include plural referents unless the context clearly dictates otherwise.

The terms "vasoactive intestinal peptide" and "VIP" refer to (SEQ ID NO:3) HSDAVFTDNYTRLRKQMAVKKY-LNSILN unless the context suggests otherwise. VIP is a multifunctional endogenous polypeptide that modulates both innate and adaptive immunity at multiple levels of immune cell differentiation and activation. There are two human isoforms of the preproprotein: human isoform 1 (SEQ ID NO:1) 1 MDTRNKAQLL VLLTLLSVLF SQT-SAWPLYR APSALRLGDR IPFEGANEPD QVSLKE-DIDM 61 LQNALAENDT PYYDVSRNAR HADGVFTSDF SKLLGQLSAK KYLESLMGKR VSS-NISEDPV 121 PVKRHSDAVF TDNYTRLRKQ MAVK-KYLNSI LNGKRSSEGE SPDFPEELEK and human isoform 2 (SEQ ID NO:2) 1 MDTRNKAQLL VLLTLLSVLF SQTSAWPLYR APSALRLGDR IPFEGANEPD QVSLKE-DIDM 61 LQNALAENDT PYYDVSRNAR HADGVFTSDF SKLLGQLSAK KYLESLMGKR VSNISEDPVP 121 VKRHSDAVFT DNYTRLRKQM AVKKYLNSIL NGKRSSEGES PDFPEELEK.

VIP is typically secreted by a variety of cells such as neurons (in both the central and peripheral nervous systems) B-cells, T-cells, and accessory cells. VIP and the closely related neuropeptide pituitary adenylyl cyclase-activating polypeptide (PACAP) bind to three known receptors—VPAC1, VPAC2, and PAC1. It is believed that T-cells and dendritic cells (DC) express VPAC1 and VPAC2, but not PAC1. PAC1 is mainly expressed on neuron and endocrine cells in the brain and pituitary and adrenal glands, and in most forms selectively binds PACAP.

In adaptive immune responses, VIP polarizes $CD4^+$ T-cells to an immunosuppressive Th2 response while suppressing the Th1 responses. T-cell activation and differentiation induce VPAC2 expression, while VPAC1 is down-regulated following stimulation of human blood T-cells with anti-CD3 monoclonal antibody plus PMA. VIP also acts on APC and regulates their function. Through the VPAC1 receptor, VIP leads to the development of bone marrow-derived tolerogenic DCs in vitro and in vivo. In a mouse model of bone marrow transplantation, DC that were differentiated in the presence of VIP, and then transplanted along with bone marrow cells and splenic T-cells induced the generation of regulatory T-cells and protected mice from acute graft versus host disease (GvHD). Th2 polarization is achieved partly through VIP regulation of costimulatory signals on antigen presenting cells (APC) and inhibition of IL-1, TNF-α, IL-6, and IL-12 production. VIP suppresses expression of the pattern recognition receptors toll-like receptor (TLR) 2 and TLR4 on APC and inhibits TLR3-signaling. Conversely, binding of ligands to TLR2, TLR4, and TLR7 down-regulate VPAC2 expression on APC.

The term "VIP antagonist" refers to any molecule that inhibits or detracts from the ability of VIP to alter immune responses. VIP antagonists are known including VIP analogues, VIP fragments, growth hormone-releasing factor analogs and hybrid peptides. A number of VIP antagonists are disclosed in U.S. Pat. Nos. 5,565,424; 7,094,755; 6,828, 304, and are all hereby incorporated by reference. Some examples of VIP antagonist include the following and variants thereof: [Ac-Tyr1,D-Phe2]GRF 1-29, amide, i.e., (SEQ ID NO:4) YFDAIFTNSYRKVLGQLSARKLLQDIMSR (Modifications: Tyr-1=N-terminal Ac, Phe-2=D-Phe, Arg-29=C-terminal amide); VIP (6-28), i.e., (SEQ ID NO: 5) FTDNYTRLRKQMAVKKYLNSILN (Modifications: Asn-23=C-terminal amide); [D-p-Cl-Phe6, Leu17]-VIP, i.e., (SEQ ID NO:6) HSDAVFTDNYTRLRKQLAVKKYLN-SILN (Modifications: Phe-6=p-Cl-D-Phe, Asn-34=C-terminal amide); VIP-hyb also known as VIPhybrid, i.e., a hybrid peptide of neurotensin and VIP consisting of an N-terminal (SEQ ID NO: 7) KPRRPY, also designated neurotensin (6-11)] followed by the C-terminal 22 amino acids of VIP, i.e., (SEQ ID NO: 8) TDNYTRLRKQMAVKKYLNSILN, also designated VIP (7-28); N-terminal Stearyl, Norleucine 17 VIPhyb, i.e., (SEQ ID NO: 9) KPRRPYTDNYTRL-RKQXAVKKYLNSILN, wherein St is Stearyl and X is norleucine; Ac His1 [D-Phe(2), Lys(15), Arg(16), Leu(27)]-VIP(1-7)/GRF(8-27), i.e., (SEQ ID NO:10) HFDAVFTNSYRKVLKRLSARKLLQDIL, C-terminal amide; and pituitary adenylate cyclase-activating polypeptide, PACAP (6-38) C-terminal amide, i.e., (SEQ ID NO:11) TDSYSRYRKQMAVKKYLAAVLGKRYKQRVKNK. It is contemplated that any of these molecules may be modified with hydrocarbon or polyethylene glycol groups in order to provide improve properties such as solubility, bioavailability, and/or biological degradation.

Sequence "identity" refers to the number of exactly matching residues (expressed as a percentage) in a sequence alignment between two sequences of the alignment. As used herein, percentage identity of an alignment is calculated using the number of identical positions divided by the greater of the shortest sequence or the number of equivalent positions excluding overhangs wherein internal gaps are counted as an equivalent position. For example the polypeptides GGGGGG and GGGGT have a sequence identity of 4 out of 5 or 80%. For example, the polypeptides GGGPPP and GGGAPPP have a sequence identity of 6 out of 7 or 85%.

Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—S T N Q.

The terms "variant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Certain variants have less than 10%, and preferably less than 5%, and still more preferably less than 2% changes (whether substitutions, deletions, and so on).

"Subject" refers any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

Antibodies

The disclosure also includes relates to a VIP antagonist antibody that specifically binds VIP or VIP receptor such as VPAC1, VPAC2, and PAC1. The disclosure should not be construed as being limited solely one type of antibody. Rather, should be construed to include antibodies that specifically bind VIP, VIP preproproteins, VIP receptors, or portions thereof. One skilled in the art would appreciate, based upon the disclosure provided herein, that the antibody can specifically bind with any portion of the polypeptide and the polypeptide can be used to generate antibodies specific. However, in certain embodiments, the disclosure is not limited to using the full-length polypeptide corresponding to VIP.

The antibodies can be produced by immunizing an animal such as, but not limited to, a rabbit or a mouse, with a protein, or a portion thereof, or by immunizing an animal using a protein comprising at least a portion of the polypeptide corresponding to VIP. One skilled in the art would appreciate, based upon the disclosure provided herein, smaller fragments of these proteins can also be used to produce antibodies that specifically bind the polypeptide.

Certain embodiments of the disclosure encompass polyclonal, monoclonal, synthetic antibodies, and the like. Moreover, the antibody can be used to detect and or measure the amount of protein present in a biological sample using well-known methods such as, but not limited to, Western blotting and enzyme-linked immunosorbent assay (ELISA). The antibody can also be used to immunoprecipitate and/or immuno-affinity purify their cognate antigen using methods well-known in the art. Thus, by administering the antibody to a cell or to the tissue of an animal, or to the animal itself, the interactions between VIP and its cognate receptor are therefore inhibited.

In another embodiment, a monoclonal antibody is obtained from the non-human animal, and then modified, e.g., humanized, deimmunized, chimeric, may be produced using recombinant DNA techniques known in the art. A variety of approaches for making chimeric antibodies have been described. See, e.g., U.S. Pat. No. 4,816,567 and U.S. Pat. No. 4,816,397. Humanized antibodies may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by U.S. Pat. No. 5,585,089; U.S. Pat. No. 5,693,761; U.S. Pat. No. 5,693,762; U.S. Pat. No. 5,859,205; and U.S. Pat. No. 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

In certain embodiments, a humanized antibody is optimized by the introduction of conservative substitutions, consensus sequence substitutions, germline substitutions and/or backmutations. An VIP antibody or antibody fragment thereof may also be modified by specific deletion of human T cell epitopes or "deimmunization" by the methods disclosed in U.S. Pat. No. 7,125,689 and U.S. Pat. No. 7,264,806. Briefly, the heavy and light chain variable domains of an antibody can be analyzed for peptides that bind to MHC Class II; these peptides represent potential T-cell epitopes. For detection of potential T-cell epitopes, a computer modeling approach termed "peptide threading" can be applied, and in addition a database of human MHC class II binding peptides can be searched for motifs present in the VH and VL sequences. These motifs bind to any of the 18 major MHC class II DR allotypes, and thus constitute potential T cell epitopes. Potential T-cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. The V BASE directory provides a comprehensive directory of human immunoglobulin variable region sequences. These sequences can be used as a source of human sequence, e.g., for framework regions and CDRs. Consensus human framework regions can also be used, e.g., as described in U.S. Pat. No. 6,300,064.

Drug Inhibition of Graft Versus Host Disease (GVHD) Following Allogeneic Hematopoietic Stem Cell Transplant (allo-HSCT)

In certain embodiments, the disclosure relates to methods disclosed herein that implement the methods reported herein.

The immune system has special mechanisms for dealing with pathogens that occupy intracellular space including cytotoxic T lymphocytes (CD8+ T cells) and helper T lymphocytes (CD4+ T cells). Major histocompatibility complexes (MHC) are molecules on the outside of cells that present pathogenic antigens for interaction with T cells receptors (TCRs) on CD8+ and CD4+ T cells.

Antigen expression cells (APCs), e.g., white blood cells (leukocytes) and dendritic cells, activate CD4+ T cells through interactions with Class II MHC molecules. Class I MHC molecules are on almost all cells of the body, including APCs, and activate CD8+ T cells. The structure of Class I and II MHC molecules differ from persons to person. However, the structure of Class I and II MHC molecules also have varying degrees amino acid sequence similarity (referred to as variant antigens) depending on the genetic profile of each individual.

Graft versus host disease (GVHD) is the deterioration of cells or tissues that are transplanted from a donor to a recipient due to the recognition by the immune system of the recipient that the cells or tissues are foreign. Thus, because Class I MHC are on more cells of the body, it is most desirable to transplant cells and tissues from people that have highest matching Class I MHC profiles followed by the highest matching Class II MHC profiles. Thus, in most transplant recipients, GVHD is due to activation of the immune system to mismatched Class II MHC molecules and other polymorphic proteins (minor histocompatibility antigens).

One option for treating cancers of the blood and bone marrow is to kill existing blood and marrow cells, e.g., through radiation or chemotherapy, and transplant similar cells from a healthy donor, referred to as an allogeneic hematopoietic stem cell transplant (allo-HSCT). Chemotherapy for bone marrow remission typically includes prednisone, vincristine, and an anthracycline drug; other drug plans may include L-asparaginase or cyclophosphamide. Another option is prednisone, L-asparaginase, and vincristine. Another options included methotrexate and 6-mercaptopurine (6-MP).

Hematopoietic cells can be obtained from suitably matched related or unrelated volunteer donors (allogeneic) or from the tissues of the subject (autologous). Sources of hematopoietic cells include the bone marrow, blood, or umbilical cord blood. One option is to obtain hematopoietic stem cells from a bone of a donor such as physically harvesting it from the pelvis. Hematopoietic stem cells (HSCs) may be obtained from peripheral blood by apheresis wherein blood is centrifuged and subsequently separated into plasma, leukocytes (white blood cells), and erythrocytes (red blood cells). The plasma typically contains HSCs and other cells such as, APCs and T-cells. Administering Granulocyte-colony stimulating factor to the donor prior to apheresis increases stem cell concentrations.

A major complication of allo-HSCT is GVHD. GVHD is believed to be due in part to stimulation of donor CD8+ T cells by APCs of the donor and recipient host through presentation of antigens in Class I MHC molecules. Exchange of membrane fragments and associated proteins between cells, termed trogocytosis, generates cross-dressed APCs. Wang et al. report that the transference of transmembrane proteins, such as MHC class I—peptide complexes, from irradiated hosts to donor dendritic cells (DCs), one from of APC cells, results in them having host antigens. See Blood. 2011, 118(24):6426-37. Cross-dressed donor DCs that acquire host MHC class I—peptide complexes are potent stimulators of T cells. CD11c is a type I transmembrane protein found at high levels on most human DCs. The presence of "cross-dressed" CD11c+ antigen presenting APCs cells expressing both donor and recipient type MHC-I molecules supports a "semi-direct" pathway of allo-activation. These APCs can efficiently present allo-antigens to both CD4+ and CD8+ T cells and activate immune responses that can lead to allograft rejection or GVHD.

The high frequencies of cross-dressed donor CD11c+ APCs following allo-HSCT indicates that semi-direct allo-antigen presentation can play an important role in the initiation of GVHD. Reducing the generation of cross-dressed APCs by pharmacological interruption of trogocytosis is an approach to reduce or prevent GVHD post allo-HSCT, targeting the semi-direct pathway of allo-antigen presentation. Data herein indicates that paclitaxel, a microtubule inhibitor, and VIPHyb, an antagonist of vasoactive intestinal peptide signaling, can reduce semi-direct presentation of allo-antigen to T cells and reduce allo-reactivity without direct cytotoxic effects.

Methods of Use

In certain embodiments, the disclosure relates to methods of treating or preventing host verses graft disease in a subject comprising administering an effective amount of a drug such as an antagonist of vasoactive intestinal peptide signaling and/or a chemotherapy agent disclosed herein to a subject that is to receive or received transplanted allogeneic tissue or cells.

In certain embodiments, the antagonist of vasoactive intestinal peptide signaling is a fragment of VIP, or VIP fragment or analog containing one or more D-amino acids disclosed herein or variant thereof. In certain embodiments, the antagonist of vasoactive intestinal peptide signaling is a protein comprising SEQ ID NO: 12 (NH2-KPRRPYTDNY-TRKQMAVKK YLNSILN-carbon terminal amide) or greater than 80%, 85%, 90%, or 95% identity or similarity thereto. In certain embodiments, the antagonist of vasoactive intestinal peptide signaling is an VIP antibody or antibody fragment with an epitope to VIP or a VIP receptor.

In certain embodiments, the subject received transplanted allogeneic hematopoietic stem cells. In certain embodiments, subject received transplanted allogeneic hematopoietic stem cells separated from peripheral blood. In certain embodiments, the subject received chemotherapy to radiation treatments prior to receiving transplanted allogeneic hematopoietic stem cells. In certain embodiments, the subject is a human.

In certain embodiments, the disclosure relates to methods of treating cancers or conditions of the blood and bone marrow comprising the steps of, exposing the subject to radiation and/or administering a chemotherapy agent to the subject; transplanting allogeneic hematopoietic stem cells into the subject; and administering an antagonist of vasoactive intestinal peptide signaling under conditions such that host verses graft disease is prevented or reduced compared to the absence of a VIP antagonist.

In certain embodiments, the cancers or conditions are selected from osteosarcoma, Ewing tumors, chordomas, chondrosarcomas, bone marrow failure, sickle cell disease, and thalassemia.

In certain embodiments, subject is further administered one or more chemotherapy agents selected from imatinib, doxorubicin, cisplatin, carboplatin, etoposide, ifosfamide, cyclophosphamide, methotrexate, vincristine.

In certain embodiments, the subject is further administered a combination of cisplatin and doxorubicin.

In certain embodiments, the cancer or conditions are selected from leukemia, lymphoma, myeloma, and myelodysplasia.

In certain embodiments, the subject is further administered a chemotherapy agent, antibodies, directed at lymphoma cells.

In certain embodiments, the disclosure relates to the use of drugs to prevent graft versus host disease (GVHD) in a subject after, before, or during a hematopoietic stem cell transplant.

In certain embodiments, the subject is administered a drug reported herein, e.g. the VIP antagonist VIPhyb, after a hematopoietic stem cell transplant. In certain embodiments, the VIP antagonist is administered for more than one month, two months, three months, four months, five months, six months, one year, one and one half year, or two years on a daily, bi-daily, or weekly basis after a hematopoietic stem cell transplant.

In certain embodiments, the subject is administered a drug reported herein, e.g. the VIP antagonist VIPhyb, before a hematopoietic stem cell transplant. In certain embodiments, the VIP antagonist is administered more than 3, hours, 5 hours, 10 hours, 24 hours, 2 days, 3 days, or 7 days, on a daily, bi-daily, or weekly basis.

EXAMPLES

Drug Inhibited Trogocytosis in MLR

Figure 1A:
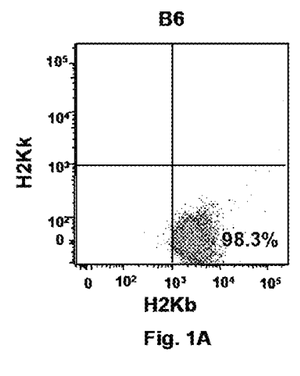
FIGS. 1A-C shows data indicating the presence of cross-dressed donor CD11c+ APCs were generated following allo-HSCT. Left and middle panels show expression of H2Kb and H2Kk in non-transplanted mice. Right panel shows cross-dressed APC on day 15 post allo-HSCT.
Figure 1B:
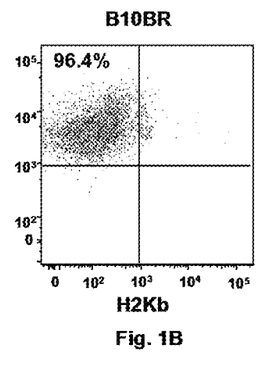
Figure 1C:
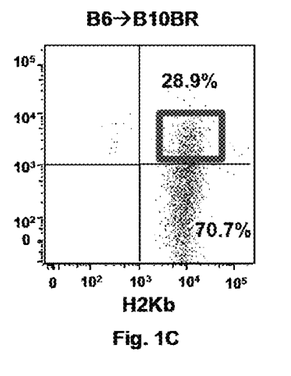

Whether drugs can inhibit cross-dressed APCs from facilitating antigen presentation to donor T cells and prevent GVHD following allo-HSCT was tested. Cross-dressed donor CD11c+ APCs were generated in vivo following allo-HSCT (FIG. 1).

Figure 2:
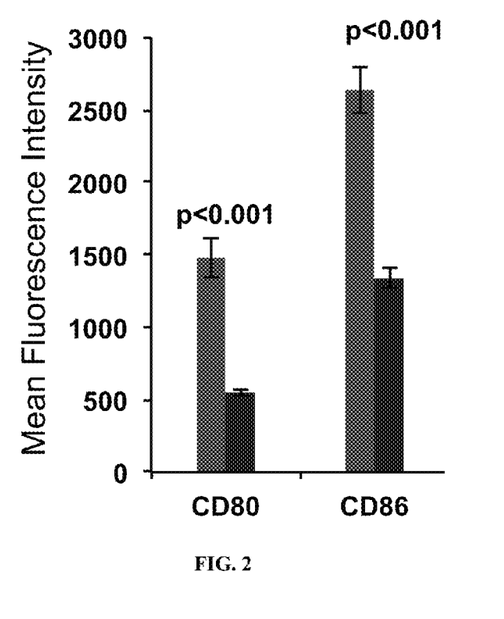
FIG. 2 shows data indicating cross-dressed APCs (red) have increased expression of co-stimulatory molecules CD80 and CD86 compared to non-cross dressed donor CD11c+ APC (blue).

Recipient spleens showed that 50%, 28.6% (p=0.01) and 12% (p=0.02) of donor type CD11c+ cells were cross dressed on days 10, 15 and 20 respectively post-transplant (n=5). These cross dressed APCs expressed higher levels of co-stimulatory molecules CD80(p<0.001) and CD86 (p<0.001), and MHC-II compared to non-cross-dressed donor CD11c+ cells (FIG. 2).

Figure 3:
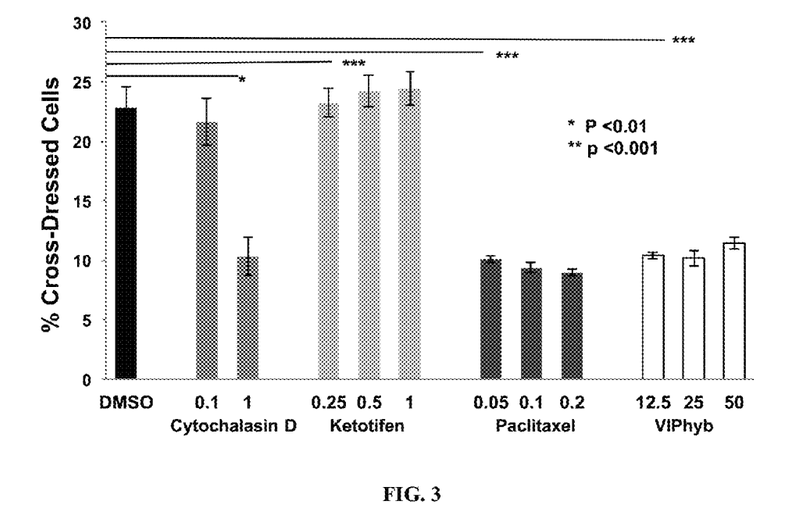
FIG. 3 shows data indicating certain drugs inhibited trogocytosis in MLR. The frequency of cross-dressed CD11c+ APC on day 6 of MLR was assessed by flow cytometry.
Figure 4A:
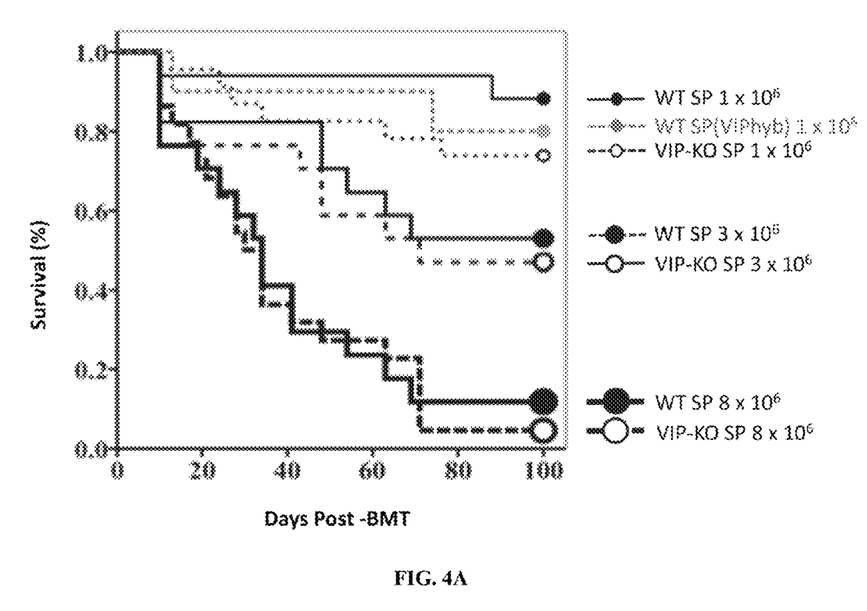
FIG. 4B shows survival GvHD clinical score, a market of graft versus host disease as described in FIG. 4A.
Figure 4B:
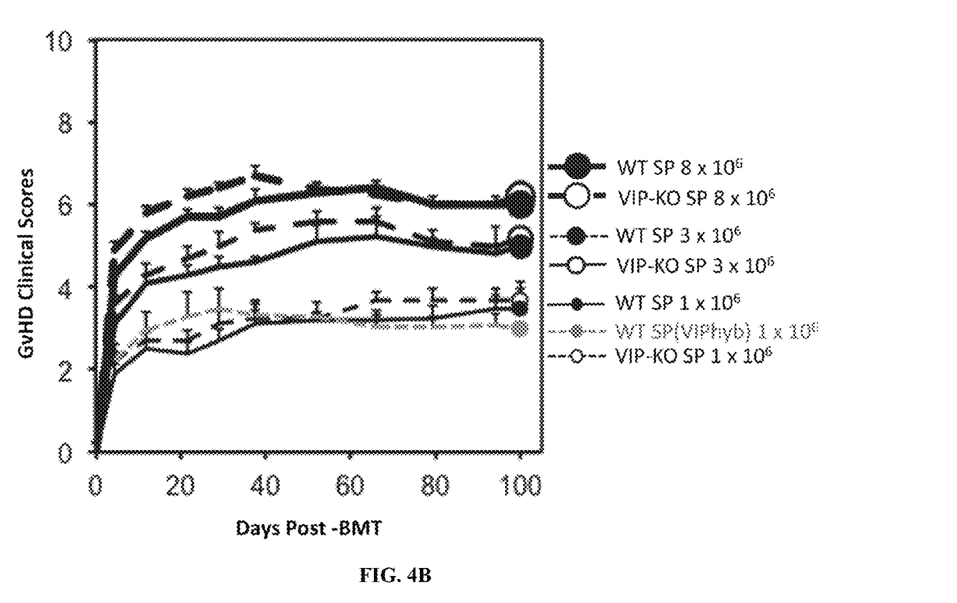
Figure 5:
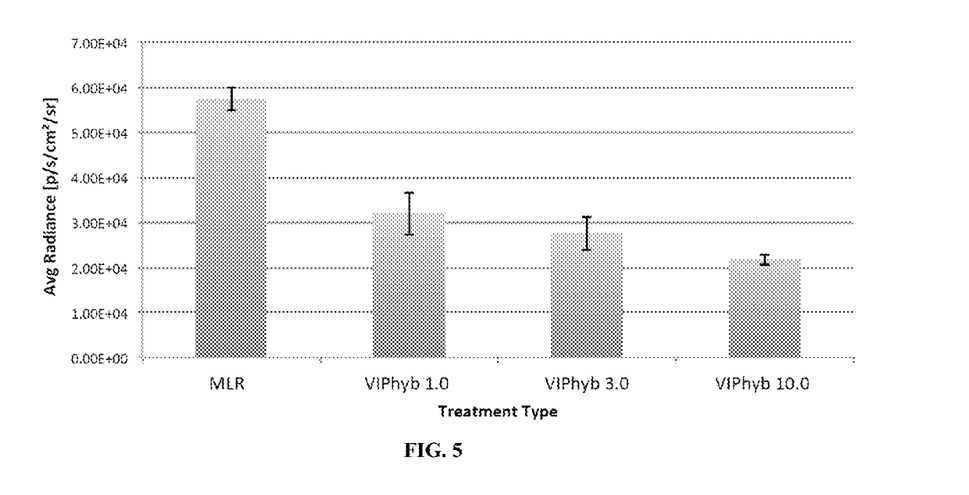
FIG. 5 shows data on metabolic activity of allo-reactive T cells in MLR as assessed by bio-luminescence imaging. Vip antagonist (VIPHyb) was added to the mixed lymphocyte cultures every day at concentrations of 1, 3 and 10 micromolar. Bioluminescent imaging was performed on Day 3. The data show reduced alloreactivity with addition of VIPHyb.

Sorted cross-dressed CD11c+ cells from recipient mice were able to induce in vitro proliferation of co-geneic CD8 T-cells, while their noncross-dressed counterparts did not. For cross-dressed CD11c+ cells that were generated in vitro, the exchange of plasma membrane fragments was inhibited in vitro by exposure to doses of paclitaxel and VIP antagonist (FIG. 3), while preserving cell viability. Furthermore, bone marrow treated with 0.05 uM of paclitaxel, caused significantly decreased T cell proliferation in primary MLR compared to non-drug treated bone marrow.

The invention claimed is:

1. A method of treating graft versus host disease in a subject comprising administering an effective amount of a protein comprising SEQ ID NO: 12 with a C-terminal amide to a subject after a hematopoietic stem cell transplant.

2. The method of claim 1 wherein the subject received transplanted allogeneic hematopoietic stem cells.

3. The method of claim 2 wherein the subject received transplanted allogeneic hematopoietic stem cells separated from peripheral blood.

4. The method of claim 2 wherein the subject received chemotherapy to radiation treatments prior to receiving transplanted allogeneic hematopoietic stem cells.

5. The method of claim 1 wherein the subject is a human.

* * * * *

SEQUENCE LISTING

<160> NUMBER OF SEQ ID NOS: 12

<210> SEQ ID NO 1
<211> LENGTH: 170
<212> TYPE: PRT
<213> ORGANISM: Homo sapiens

<400> SEQUENCE: 1

```
Met Asp Thr Arg Asn Lys Ala Gln Leu Leu Val Leu Leu Thr Leu Leu
1               5                   10                  15

Ser Val Leu Phe Ser Gln Thr Ser Ala Trp Pro Leu Tyr Arg Ala Pro
            20                  25                  30

Ser Ala Leu Arg Leu Gly Asp Arg Ile Pro Phe Glu Gly Ala Asn Glu
        35                  40                  45

Pro Asp Gln Val Ser Leu Lys Glu Asp Ile Asp Met Leu Gln Asn Ala
    50                  55                  60

Leu Ala Glu Asn Asp Thr Pro Tyr Tyr Asp Val Ser Arg Asn Ala Arg
65                  70                  75                  80

His Ala Asp Gly Val Phe Thr Ser Asp Phe Ser Lys Leu Leu Gly Gln
                85                  90                  95

Leu Ser Ala Lys Lys Tyr Leu Glu Ser Leu Met Gly Lys Arg Val Ser
            100                 105                 110

Ser Asn Ile Ser Glu Asp Pro Val Pro Val Lys Arg His Ser Asp Ala
        115                 120                 125

Val Phe Thr Asp Asn Tyr Thr Arg Leu Arg Lys Gln Met Ala Val Lys
    130                 135                 140

Lys Tyr Leu Asn Ser Ile Leu Asn Gly Lys Arg Ser Ser Glu Gly Glu
145                 150                 155                 160
```

Ser Pro Asp Phe Pro Glu Glu Leu Glu Lys
            165                 170

<210> SEQ ID NO 2
<211> LENGTH: 169
<212> TYPE: PRT
<213> ORGANISM: Homo sapiens

<400> SEQUENCE: 2

Met Asp Thr Arg Asn Lys Ala Gln Leu Val Leu Thr Leu Leu
1               5                   10                  15

Ser Val Leu Phe Ser Gln Thr Ser Ala Trp Pro Leu Tyr Arg Ala Pro
            20                  25                  30

Ser Ala Leu Arg Leu Gly Asp Arg Ile Pro Phe Glu Gly Ala Asn Glu
            35                  40                  45

Pro Asp Gln Val Ser Leu Lys Glu Asp Ile Asp Met Leu Gln Asn Ala
        50                  55                  60

Leu Ala Glu Asn Asp Thr Pro Tyr Tyr Asp Val Ser Arg Asn Ala Arg
65                  70                  75                  80

His Ala Asp Gly Val Phe Thr Ser Asp Phe Ser Lys Leu Leu Gly Gln
                85                  90                  95

Leu Ser Ala Lys Lys Tyr Leu Glu Ser Leu Met Gly Lys Arg Val Ser
            100                 105                 110

Asn Ile Ser Glu Asp Pro Val Pro Val Lys Arg His Ser Asp Ala Val
            115                 120                 125

Phe Thr Asp Asn Tyr Thr Arg Leu Arg Lys Gln Met Ala Val Lys Lys
        130                 135                 140

Tyr Leu Asn Ser Ile Leu Asn Gly Lys Arg Ser Ser Glu Gly Glu Ser
145                 150                 155                 160

Pro Asp Phe Pro Glu Glu Leu Glu Lys
            165

<210> SEQ ID NO 3
<211> LENGTH: 28
<212> TYPE: PRT
<213> ORGANISM: Homo sapiens

<400> SEQUENCE: 3

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 4
<211> LENGTH: 29
<212> TYPE: PRT
<213> ORGANISM: Homo sapiens

<400> SEQUENCE: 4

Tyr Phe Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25

<210> SEQ ID NO 5
<211> LENGTH: 23
<212> TYPE: PRT
<213> ORGANISM: Homo sapiens

<400> SEQUENCE: 5

-continued

Phe Thr Asp Asn Tyr Thr Arg Leu Arg Lys Gln Met Ala Val Lys Lys
1               5                   10                  15

Tyr Leu Asn Ser Ile Leu Asn
            20

<210> SEQ ID NO 6
<211> LENGTH: 28
<212> TYPE: PRT
<213> ORGANISM: Homo sapiens

<400> SEQUENCE: 6

His Ser Asp Ala Val Phe Thr Asp Asn Tyr Thr Arg Leu Arg Lys Gln
1               5                   10                  15

Leu Ala Val Lys Lys Tyr Leu Asn Ser Ile Leu Asn
            20                  25

<210> SEQ ID NO 7
<211> LENGTH: 6
<212> TYPE: PRT
<213> ORGANISM: Homo sapiens

<400> SEQUENCE: 7

Lys Pro Arg Arg Pro Tyr
1               5

<210> SEQ ID NO 8
<211> LENGTH: 22
<212> TYPE: PRT
<213> ORGANISM: Homo sapiens

<400> SEQUENCE: 8

Thr Asp Asn Tyr Thr Arg Leu Arg Lys Gln Met Ala Val Lys Lys Tyr
1               5                   10                  15

Leu Asn Ser Ile Leu Asn
            20

<210> SEQ ID NO 9
<211> LENGTH: 28
<212> TYPE: PRT
<213> ORGANISM: Homo sapiens
<220> FEATURE:
<221> NAME/KEY: misc_feature
<222> LOCATION: (17)..(17)
<223> OTHER INFORMATION: Xaa can be any naturally occurring amino acid

<400> SEQUENCE: 9

Lys Pro Arg Arg Pro Tyr Thr Asp Asn Tyr Thr Arg Leu Arg Lys Gln
1               5                   10                  15

Xaa Ala Val Lys Lys Tyr Leu Asn Ser Ile Leu Asn
            20                  25

<210> SEQ ID NO 10
<211> LENGTH: 27
<212> TYPE: PRT
<213> ORGANISM: Homo sapiens

<400> SEQUENCE: 10

His Phe Asp Ala Val Phe Thr Asn Ser Tyr Arg Lys Val Leu Lys Arg
1               5                   10                  15

Leu Ser Ala Arg Lys Leu Leu Gln Asp Ile Leu
            20                  25

```
<210> SEQ ID NO 11
<211> LENGTH: 32
<212> TYPE: PRT
<213> ORGANISM: Homo sapiens

<400> SEQUENCE: 11

Thr Asp Ser Tyr Ser Arg Tyr Arg Lys Gln Met Ala Val Lys Lys Tyr
1               5                   10                  15

Leu Ala Ala Val Leu Gly Lys Arg Tyr Lys Gln Arg Val Lys Asn Lys
            20                  25                  30

<210> SEQ ID NO 12
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: NH2 is an amine group
<220> FEATURE:
<221> NAME/KEY: MISC_FEATURE
<222> LOCATION: (27)..(27)
<223> OTHER INFORMATION: has a carbon terminal amide

<400> SEQUENCE: 12

Lys Pro Arg Arg Pro Tyr Thr Asp Asn Tyr Thr Arg Lys Gln Met Ala
1               5                   10                  15

Val Lys Lys Tyr Leu Asn Ser Ile Leu Asn
            20                  25
```